United States Patent
Martin et al.

(10) Patent No.: US 10,357,066 B2
(45) Date of Patent: Jul. 23, 2019

(54) SYSTEM AND METHOD FOR APPAREL IDENTIFICATION

(71) Applicant: Under Armour, Inc., Baltimore, MD (US)

(72) Inventors: John Martin, Austin, TX (US); Daniel Sargeant, Austin, TX (US); F. Grant Kovach, Baltimore, MD (US); Gamir Shrestha, Austin, TX (US)

(73) Assignee: Under Armour, Inc., Baltimore, MD (US)

( * ) Notice: Subject to any disclaimer, the term of this patent is extended or adjusted under 35 U.S.C. 154(b) by 0 days.

(21) Appl. No.: 15/670,324

(22) Filed: Aug. 7, 2017

(65) Prior Publication Data
US 2019/0037932 A1 Feb. 7, 2019

(51) Int. Cl.
*G08B 23/00* (2006.01)
*A41D 1/00* (2018.01)
*A61B 5/00* (2006.01)

(52) U.S. Cl.
CPC ............ *A41D 1/005* (2013.01); *A61B 5/0002* (2013.01); *A61B 5/6804* (2013.01)

(58) Field of Classification Search
CPC ...... A41D 1/005; A61B 5/0002; A61B 5/6804
USPC ...................................................... 340/573.1
See application file for complete search history.

(56) References Cited

U.S. PATENT DOCUMENTS

| 5,524,184 A * | 6/1996 | Johnson ............... G06K 1/121 358/1.15 |
| 6,289,743 B1 * | 9/2001 | Norton .................. A43D 1/00 73/847 |
| 8,459,126 B2 * | 6/2013 | Chen .................. G01M 99/007 73/847 |
| 8,660,897 B2 | 2/2014 | Abhyanker |
| 8,676,541 B2 | 3/2014 | Schrock et al. |
| 8,739,639 B2 | 6/2014 | Owings et al. |
| 8,827,815 B2 | 9/2014 | Burroughs et al. |
| 8,988,241 B2 | 3/2015 | Tilvis et al. |
| 8,990,048 B2 | 3/2015 | Czaja et al. |
| 9,043,004 B2 | 5/2015 | Casillas et al. |
| 9,082,025 B2 | 7/2015 | Fastert et al. |
| 9,089,182 B2 | 7/2015 | Schrock et al. |
| 9,095,251 B2 | 8/2015 | Purks et al. |
| 9,192,816 B2 | 11/2015 | Molyneux et al. |

(Continued)

*Primary Examiner* — Zhen Y Wu
(74) *Attorney, Agent, or Firm* — Maginot, Moore & Beck LLP

(57) ABSTRACT

System and method for apparel identification using a scannable code. In one embodiment, the method comprises: receiving a purchase order comprising information relating to a unique identity of the apparel; printing a machine-readable code including the information relating to the unique identity onto a tag; disposing an electronic apparatus on the apparel during manufacture; attaching the tag onto a portion of the apparel during the manufacture; performing tests to the functionality of the electronic apparatus; scanning the machine-readable code of the tag during the manufacture; transmitting the information relating to the unique identity to the electronic apparatus; and providing the apparel having the information relating to the unique identity stored at the electronic apparatus to a user based on the purchase order. In one variant, the apparel comprises a shoe and the electronic apparatus comprises a movement sensor.

19 Claims, 7 Drawing Sheets

(56) References Cited

U.S. PATENT DOCUMENTS

| | | | |
|---|---|---|---|
| 9,192,817 B2 | 11/2015 | Frolov | |
| 9,262,633 B1* | 2/2016 | Todeschini | G06F 21/56 |
| 9,279,734 B2 | 3/2016 | Walker | |
| 9,282,893 B2 | 3/2016 | Longinotti-Buitoni et al. | |
| 9,381,420 B2 | 7/2016 | Burroughs | |
| 9,446,287 B2 | 9/2016 | Weast et al. | |
| 9,468,835 B2 | 10/2016 | Martikka et al. | |
| 9,498,128 B2 | 11/2016 | Jayalath et al. | |
| 9,500,464 B2 | 11/2016 | Coza | |
| 9,549,585 B2 | 1/2017 | Amos et al. | |
| 9,555,286 B2 | 1/2017 | Martikka et al. | |
| 9,600,995 B2 | 3/2017 | Gaidar et al. | |
| 9,616,290 B2 | 4/2017 | Purks et al. | |
| 9,616,291 B2 | 4/2017 | Martikka et al. | |
| 9,673,864 B2 | 6/2017 | Czaja | |
| 9,677,928 B2 | 6/2017 | Lightstone | |
| 2003/0084007 A1* | 5/2003 | Brookner | G07B 17/00508 705/408 |
| 2003/0113151 A1* | 6/2003 | Yokoyama | G09F 3/0297 400/103 |
| 2003/0187538 A1* | 10/2003 | Somaia | G06Q 30/06 700/140 |
| 2004/0024645 A1* | 2/2004 | Potter | A43D 3/02 705/26.43 |
| 2005/0086132 A1* | 4/2005 | Kanitz | G06Q 10/08 705/28 |
| 2006/0255140 A1* | 11/2006 | Jusas | G06K 5/02 235/451 |
| 2006/0261161 A1* | 11/2006 | Murofushi | G06Q 20/20 235/383 |
| 2007/0266763 A1* | 11/2007 | Therrio | A43D 999/00 73/12.01 |
| 2008/0167580 A1* | 7/2008 | Avni | A43B 3/0005 600/587 |
| 2010/0203829 A1 | 8/2010 | Granqvist et al. | |
| 2011/0303468 A1* | 12/2011 | Ting | G01G 19/4144 177/25.15 |
| 2012/0181330 A1* | 7/2012 | Kim | G06Q 30/02 235/375 |
| 2012/0234111 A1 | 9/2012 | Molyneux et al. | |
| 2012/0312605 A1* | 12/2012 | Teraoka | G01G 19/4144 177/25.14 |
| 2013/0066448 A1* | 3/2013 | Alonso | H04Q 9/00 700/91 |
| 2013/0121743 A1* | 5/2013 | Ishii | B41J 3/4075 400/613 |
| 2013/0206842 A1* | 8/2013 | Raz | G06K 19/02 235/488 |
| 2013/0213144 A1 | 8/2013 | Rice et al. | |
| 2013/0213146 A1 | 8/2013 | Amos et al. | |
| 2013/0213147 A1 | 8/2013 | Rice et al. | |
| 2013/0324274 A1 | 12/2013 | Stites | |
| 2014/0012764 A1* | 1/2014 | Kruglick | G06Q 10/0833 705/308 |
| 2014/0180866 A1* | 6/2014 | Gonzales | A43D 3/04 705/26.7 |
| 2014/0222173 A1 | 8/2014 | Giedwoyn et al. | |
| 2014/0336796 A1 | 11/2014 | Agnew | |
| 2015/0026074 A1* | 1/2015 | Cotten | G06Q 30/012 705/302 |
| 2015/0076220 A1* | 3/2015 | Nelson | G09F 3/04 235/375 |
| 2015/0148619 A1 | 5/2015 | Berg et al. | |
| 2015/0177939 A1 | 6/2015 | Anderson et al. | |
| 2015/0182841 A1 | 7/2015 | Martikka et al. | |
| 2015/0291302 A1* | 10/2015 | McNestry | B65C 9/1865 156/64 |
| 2015/0335947 A1 | 11/2015 | Kaushansky | |
| 2016/0011091 A1* | 1/2016 | Huang | G01N 3/24 73/841 |
| 2016/0016041 A1 | 1/2016 | Giedwoyn et al. | |
| 2016/0038980 A1* | 2/2016 | Nichols | G06F 16/51 209/44.1 |
| 2016/0058133 A1 | 3/2016 | Fournier | |
| 2016/0067584 A1* | 3/2016 | Giedwoyn | A61B 5/112 700/91 |
| 2016/0140574 A1* | 5/2016 | Pacotto | G09F 3/00 705/318 |
| 2016/0150854 A1* | 6/2016 | Hockerson | A43B 13/186 36/28 |
| 2016/0153853 A1 | 6/2016 | Brenner et al. | |
| 2016/0166880 A1 | 6/2016 | Nakajima | |
| 2016/0174663 A1* | 6/2016 | Le | A43D 1/00 73/818 |
| 2016/0217418 A1* | 7/2016 | Stutzbach | G06Q 10/087 |
| 2016/0242698 A1 | 8/2016 | Repka et al. | |
| 2016/0244311 A1* | 8/2016 | Burks | B67D 1/0888 |
| 2016/0250517 A1 | 9/2016 | Tilvis et al. | |
| 2016/0253892 A1* | 9/2016 | Hyde | G08B 21/18 340/686.1 |
| 2016/0262485 A1 | 9/2016 | Walker | |
| 2016/0303426 A1 | 10/2016 | Martikka et al. | |
| 2016/0307093 A1 | 10/2016 | Hsu | |
| 2016/0308583 A1 | 10/2016 | Hsu | |
| 2016/0321601 A1* | 11/2016 | Kim | G06Q 10/083 |
| 2016/0332025 A1 | 11/2016 | Repka | |
| 2016/0346617 A1 | 12/2016 | Srugo et al. | |
| 2016/0357240 A1* | 12/2016 | Oleson | G06F 1/163 |
| 2017/0056748 A1 | 3/2017 | Crawford et al. | |
| 2017/0064502 A1 | 3/2017 | Stone et al. | |
| 2017/0069191 A1 | 3/2017 | Erkkila | |
| 2017/0076619 A1 | 3/2017 | Wallach et al. | |
| 2017/0085296 A1 | 3/2017 | Hsu | |
| 2017/0086710 A1 | 3/2017 | Hamaguchi et al. | |
| 2017/0095692 A1 | 4/2017 | Chang et al. | |
| 2017/0100300 A1 | 4/2017 | Rapp et al. | |
| 2017/0100632 A1 | 4/2017 | Castelo Branco et al. | |
| 2017/0103669 A1 | 4/2017 | Silveratawil et al. | |
| 2017/0106241 A1 | 4/2017 | Kim et al. | |
| 2017/0124446 A1* | 5/2017 | Andry | G06K 19/0775 |
| 2017/0154505 A1 | 6/2017 | Kim | |
| 2017/0181703 A1 | 6/2017 | Kaib et al. | |
| 2017/0188664 A1* | 7/2017 | Manz | A43D 86/00 |
| 2017/0189751 A1 | 7/2017 | Knickerbocker et al. | |
| 2017/0189756 A1 | 7/2017 | Brothers et al. | |
| 2017/0189757 A1 | 7/2017 | Brothers et al. | |
| 2017/0193140 A1 | 7/2017 | Brothers et al. | |
| 2017/0213382 A1 | 7/2017 | Torvinen et al. | |
| 2017/0215765 A1 | 8/2017 | Amos et al. | |
| 2017/0340067 A1* | 11/2017 | Dyckmans | A43B 9/12 |
| 2017/0347745 A1* | 12/2017 | Figur | A43B 3/0084 |
| 2018/0075498 A1* | 3/2018 | Itwaru | G06Q 30/04 |
| 2018/0132559 A1* | 5/2018 | Jacobsen | A43B 13/20 |

* cited by examiner

US 10,357,066 B2

SYSTEM AND METHOD FOR APPAREL IDENTIFICATION

COPYRIGHT

A portion of the disclosure of this patent document contains material that is subject to copyright protection. The copyright owner has no objection to the facsimile reproduction by anyone of the patent document or the patent disclosure, as it appears in the Patent and Trademark Office patent files or records, but otherwise reserves all copyright rights whatsoever.

FIELD

This disclosure relates generally to the field of apparel identification via utilization of scannable codes printed on fabric tags. In one embodiment, the tags may include one or more unique identifiers pulled from a purchase order associated to the apparel. More particularly, the present disclosure relates to systems, computer programs, devices, and methods for: (i) utilizing scannable tags to enable an association of a unique item identity to an electronic component of an item of apparel; and (ii) enabling association of the item of apparel to a user's profile in a health monitoring application run at a user device via the electronic component of the item of apparel broadcasting the unique identity stored therein.

BACKGROUND

In recent years, so-called "smart" apparel that is worn by users to measure or track physical and physiological information relating to the health and activity levels of the users have gained great popularity. Such "smart" apparel comprises one or more sensors to sense health data relating to a user, including exercise data, and provide the data to one or more health monitoring devices or applications to be stored, processed, and displayed to the user. Common health data analysis systems provide displays of information relating to the user's health goals, diet advice or analysis, and exercise advice or analysis, etc. based on the collected health data. Specifically, a health data analysis system may maintain a record of and display a user's activity log over a period of time.

As smart apparel becomes more ubiquitous additional processes are needed to ensure manufacture and testing thereof proceed swiftly. Moreover, additional mechanisms are needed to enable connection between a user's health monitoring device or application and the "smart" apparel.

SUMMARY

The present disclosure addresses the foregoing needs by disclosing, inter alia, methods, devices, systems, and computer programs for (i) utilizing scannable tags to enable an association of a unique item identity to an electronic component of an item of apparel; and (ii) enabling association of the item of apparel to a user's profile in a health monitoring application run at a user device via the electronic component of the item of apparel broadcasting the unique identity stored therein.

In one aspect of the disclosure, a method of enabling shoe identification is disclosed. In one embodiment, the method comprises: (i) receiving data used to create a machine-readable label comprising at least information relating to a unique identity of one or more of a pair of shoes; (ii) using the data to cause a printer to print a fabric tag comprising at least the machine-readable label; (iii) disposing at least one sensor on the one or more of the pair of shoes during manufacture thereof; (iv) attaching the fabric tag onto a portion of the one or more of the pair of shoes during the manufacture thereof; (v) scanning the machine-readable label of the fabric tag during the manufacture of the pair of shoes, the act of scanning causing the information relating to the unique identity to be written to storage at the at least one sensor; and (vi) providing the pair of shoes to a user.

In another aspect of the disclosure, a system for enabling apparel identification is disclosed. In one embodiment, the system comprises: (i) a code scanning apparatus configured to scan a machine-readable code printed onto a tag, the tag being attached to an item of apparel, the code comprising at least information relating to a unique identity of the item of apparel; (ii) a storage component configured to at least temporarily store the information relating to the unique identity of the item of apparel received via the scanning apparatus; (iii) an apparel receiving apparatus configured to receive the item of apparel for testing; and (iv) a processor in communication with the storage component and the apparel receiving apparatus and configured to execute at least one computer application thereon, said computer application comprising a plurality of instructions which are configured to, when executed, cause the apparel receiving apparatus to: perform one or more tests with respect to the item of apparel while the item of apparel is received within the apparel receiving component; and cause the information relating to the unique identity of the item of apparel to be written to a memory of an electronic component of the item of apparel.

In yet another aspect of the disclosure, a method of enabling identification of an article of apparel is disclosed. In one embodiment, the method comprises: (i) receiving a purchase order comprising information relating to a unique identity of the article of apparel; (ii) printing a machine-readable code comprising at least the information relating to the unique identity of the article of apparel onto a tag; (iii) disposing at least one electronic apparatus on the article of apparel during manufacture thereof; (iv) attaching the tag onto a portion of the article of apparel during the manufacture thereof; (v) performing one or more tests to the functionality of the at least one electronic apparatus; (vi) scanning the machine-readable code of the tag during the manufacture of the article of apparel; (vii) transmitting the information relating to the unique identity to the at least one electronic apparatus; and (viii) providing the article of apparel having the information relating to the unique identity stored at the at least one electronic apparatus to a user based on the purchase order.

These and other aspects of the disclosure shall become apparent when considered in light of the disclosure provided herein.

Figure 1:
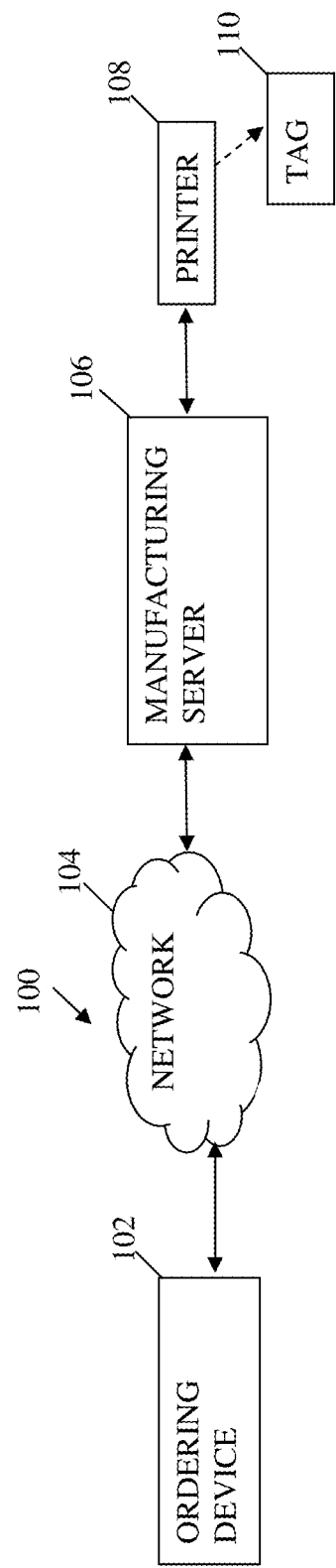
FIG. 1 is a block diagram illustrating an exemplary system for generating tags for apparel having scannable codes printed thereon in accordance with one embodiment of the present disclosure.

All Figures © Under Armour, Inc. 2017. All rights reserved.

DETAILED DESCRIPTION

Disclosed embodiments include systems, apparatus, methods and storage media which (i) utilize scannable tags to enable an association of a unique item identity to an electronic component of an item of apparel; and (ii) enable association of the item of apparel to a user's profile in a health monitoring application run at a user device via the electronic component of the item of apparel broadcasting the unique identity stored therein.

In the following detailed description, reference is made to the accompanying drawings which form a part hereof wherein like numerals designate like parts throughout, and in which is shown, by way of illustration, embodiments that may be practiced. It is to be understood that other embodiments may be utilized, and structural or logical changes may be made without departing from the scope of the present disclosure. Therefore, the following detailed description is not to be taken in a limiting sense, and the scope of embodiments is defined by the appended claims and their equivalents.

Aspects of the disclosure are disclosed in the accompanying description. Alternate embodiments of the present disclosure and their equivalents may be devised without parting from the spirit or scope of the present disclosure. It should be noted that any discussion herein regarding "one embodiment", "an embodiment", "an exemplary embodiment", and the like indicate that the embodiment described may include a particular feature, structure, or characteristic, and that such particular feature, structure, or characteristic may not necessarily be included in every embodiment. In addition, references to the foregoing do not necessarily comprise a reference to the same embodiment. Finally, irrespective of whether it is explicitly described, one of ordinary skill in the art would readily appreciate that each of the particular features, structures, or characteristics of the given embodiments may be utilized in connection or combination with those of any other embodiment discussed herein.

Various operations may be described as multiple discrete actions or operations in turn, in a manner that is most helpful in understanding the claimed subject matter. However, the order of description should not be construed as to imply that these operations are necessarily order dependent. In particular, these operations may not be performed in the order of presentation. Operations described may be performed in a different order than the described embodiment. Various additional operations may be performed and/or described operations may be omitted in additional embodiments.

For the purposes of the present disclosure, the phrase "A and/or B" means (A), (B), or (A and B). For the purposes of the present disclosure, the phrase "A, B, and/or C" means (A), (B), (C), (A and B), (A and C), (B and C), or (A, B and C). Similar logic applies to the use of the term "or" herein; i.e., "A or B" means (A), (B), or (A and B).

The terms "comprising," "including," "having," and the like, as used with respect to embodiments of the present disclosure, are synonymous.

Network Architecture

Referring now to FIG. 1, an exemplary system 100 for generating tags for apparel having scannable codes printed thereon is shown. As illustrated, the system generally comprises a purchasing or ordering device 102 in communication a manufacturing server 106 via a network 104.

The ordering device 102 comprises any computerized apparatus which enables a user to place an order for apparel. For example, the ordering device 102 may comprise a wired or wireless device which accesses available apparel for purchase via a website (e.g., www.underarmour.com), such as a smart phone, a laptop computer, tablet computer, etc. Alternatively, the ordering device 102 may comprise a traditional telephone by which a user calls a customer service representative to purchase apparel. As will be discussed in further detail below, the telephone purchase embodiment may require an intermediary server (not shown). Additional or alternative embodiments (discussed elsewhere herein) may further require the use of an intermediary server as well. The apparel may comprise clothing, shoes, socks, arm bands, chest bands, head bands, gloves, hats, or any other item to be worn by a user. For purposes of the present disclosure, and as discussed in further detail below, the apparel comprises so-called "smart" apparel; i.e., having one or more electronic devices or components, processors, memory, and/or sensors associated therewith, attached thereto, and/or integrated therein.

The network 104 which enables communication between the ordering device 102 and the manufacturing server 106 may comprise one or more wired and/or wireless, private and/or public network, including but not limited to, e.g., the Internet. The network 104 is, for example, a wireless local area network (WLAN), a wireless wide area network (WWAN), a wired network, or any other suitable communication channel. Accordingly, the ordering device 102 and the manufacturing server 106 are configured with appropriate networking communication interfaces. An example of wired communication interface may include, but is not limited to, Ethernet; while examples of wireless communication interfaces may include, but are not limited to, near field communication (NFC), Bluetooth, Wi-Fi, 4G or 5G LTE. It is further appreciated that various gateways, routers, switches, base stations, and so forth may be involved in facilitating and forwarding communication between the foregoing devices. Additionally, it is noted that the foregoing network may comprise several networks, such that the described components are distributed in various ones thereof. In alternative embodiments software via software API's.

The manufacturing server 106 comprises a computerized apparatus configured to receive information from the purchasing device 102. In one variant, the information received from the purchasing device 102 comprises at least a portion of information associated to a purchase order for the purchase of apparel. According to this variant, a user uses the ordering device 102 to enter an order for apparel, the order may include apparel-related information (such as item identification number, color identification, size, etc.), user-related information (such as credit card number, billing and shipping addresses, etc.), and purchase order-related information (such as purchase order number and purchase order date).

In one embodiment, the manufacturing server 106 receives all of the order information, including e.g., the apparel-related information, the user-related information, and the purchase order-related information. The information is then parsed to identify only that information which is utilized to create an apparel tag as discussed herein. In one particular example, only the purchase order date, purchase order number, model identification, color identification, size, and serial number are utilized. However, other data and/or combinations of data may be utilized with equal success. The remainder of the apparel data, user data, and purchase order data may be stored, such as at a network storage apparatus (not shown).

In another embodiment, the entirety of the apparel data, user data, and purchase order data are first provided to a network server (not shown), which parses the data into two categories: (i) that which is necessary to generate the apparel tag, and (ii) that which is not. Then, according to this embodiment, the portion of the data which is necessary for generation of the apparel tag is provided to the manufacturing server 106 for generation thereof.

In one specific implementation, the manufacturing server 106 uses the portion of purchase order data to create a data string or code which defines a scannable code (such as a bar code, QR code, 2-D matrix, etc.). As illustrated in FIG. 1, the manufacturing server 106 provides the data string or code to a printer 108 which is configured to print the apparel tag 110. The tag 110 will be discussed with respect to FIG. 2 below.

Figure 2:
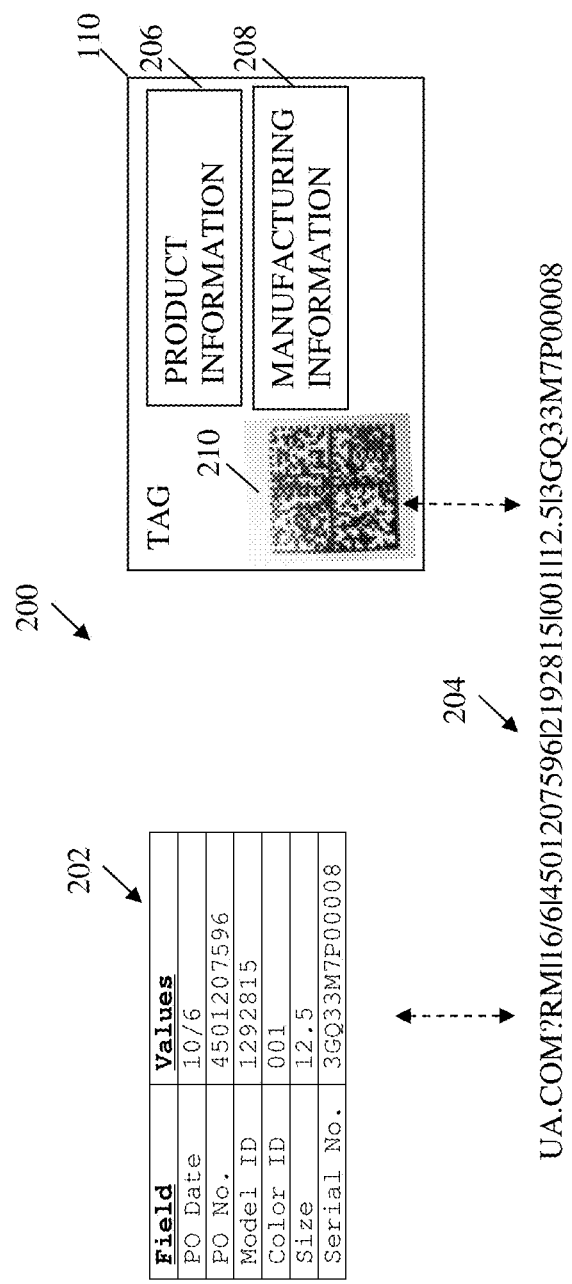
FIG. 2 is graphic representation illustrating the association of aspects and values therefor to an apparel tag in accordance with one embodiment of the present disclosure.

As shown in FIG. 2, the apparel tag 110 demonstrates exemplary associations 200 between data fields (and their values 202 in the purchase order) to data defining a scannable code 204. As specifically shown in this example, the purchase order date (or "PO Date") is October 6 or 10/6; the purchase order number (or "PO No.") is 4501207596. The purchase order date is the date on which the order to purchase the apparel is completed; the purchase order number is a unique number assigned to the purchase order for tracking purposes. The purchase order number may be assigned by the manufacturing server 106 or a network server (not show) during the purchasing process. The illustrated example further indicates an apparel model (Model ID) of 1292815; the color is identified as Color ID 001; and the size is identified as 12.5. The model identifier comprises the unique identification number assigned to a given article of apparel by the manufacturer, distributor, and/or seller. Each apparel model is associated with a plurality of available colors or color combinations and sizes. The serial number associated to the apparel is also provided, the serial number is the particular identifier for one single item of apparel. Each item of apparel is giving a serial number in a similar manner as a vehicle identification number (VIN); in the illustrated example, the serial number is given as 3GQQ33M7P00008. These values are converted to a data string or code 204 as illustrated. In one variant, the data string 204 is given in a uniform or standard format. In the given example, the standard format is:

Point of purchase|PO Date|PO No.|Model ID|Color ID|Size|Serial No.

Although not illustrated in the table of values 202 of FIG. 2, the illustrated example is made from a website purchase, in this case, underarmour.com. Therefore, the point of purchase portion of the standard format for the data string 204 includes an indicator of the web address (UA.COM). It is appreciated that the specific values and example fields given in FIG. 2 are merely illustrative of the general concepts provided herein; other values, fields, formats, aspects and/or characterizations may be utilized with equal success.

The illustration of FIG. 2 further provides one exemplary apparel tag 110 generated from the data 204. As shown, the apparel tag 110 comprises a scannable code 210, as well as product information 206 (optional), and manufacturing information 208 (optional). In one exemplary embodiment, the product information 206 may comprise a trademark or other company identifier, reference information such as size, style identifier, etc. In another exemplary embodiment, the manufacturing information 208 may comprise a country of manufacture, a description of materials used in construction, laundering or care instructions, etc. The tag 110 may be printed onto a fabric for incorporation onto a fabric portion of the item of apparel (i.e., a fabric tag); alternatively the tag may be printed onto a thin plastic, sticker, or other material.

Referring back again to FIG. 1, the system 100 provides a mechanism whereby the user's entry of details relating to the purchase of apparel are utilized to create an apparel tag that uniquely identifies the item of apparel. Although not illustrated, the apparel tag is attached to the item of apparel to which it relates. In other words, the apparel tag is attached to the item of apparel which the user ordered according to the purchase order. As noted above, it is the purchase order which contained the data used to generate the tag. Systems for utilizing the tag are illustrated in FIG. 3 and described below.

Figure 3:
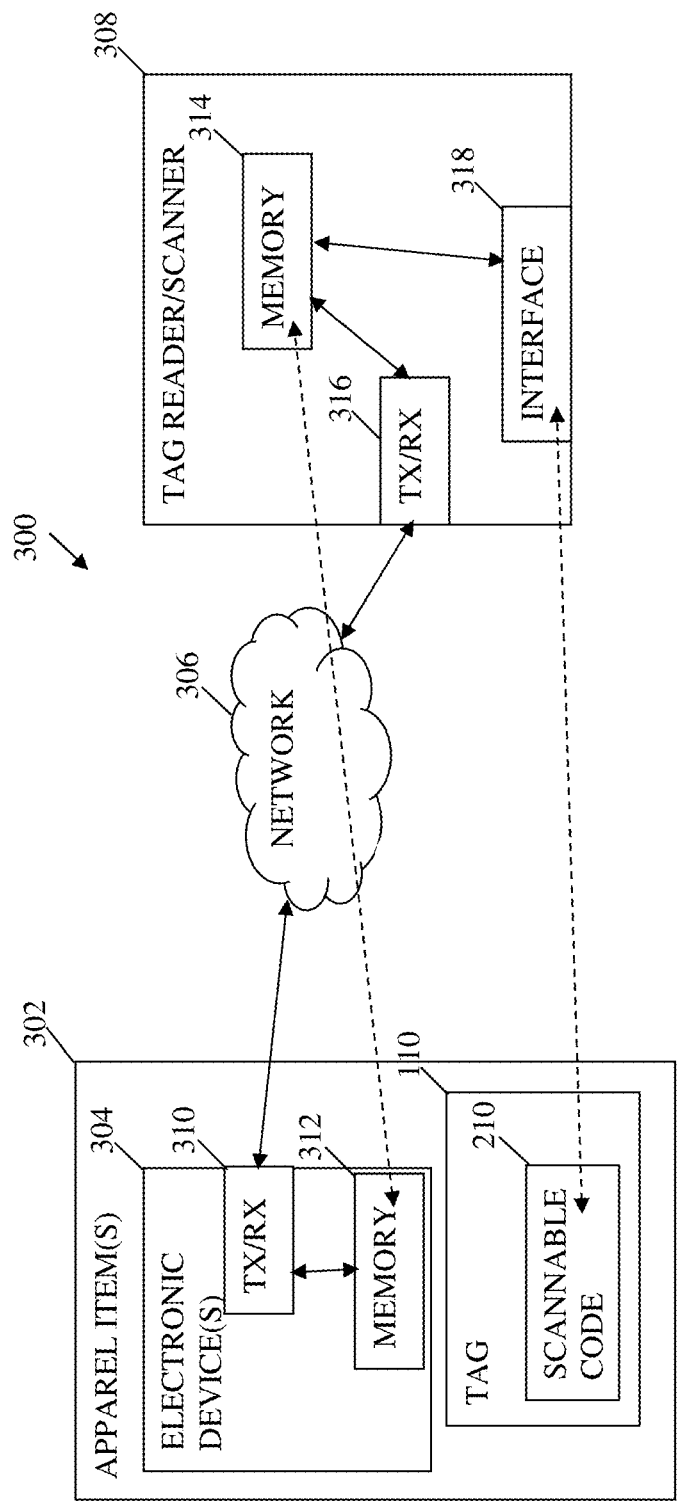
FIG. 3 is a block diagram illustrating an exemplary system for automatically associating data contained within the apparel tag to one or more electronic devices of an apparel item in accordance with one embodiment of the present disclosure.

Referring now to FIG. 3, an exemplary system 300 for automatically associating data contained within the apparel tag to one or more electronic devices of an apparel item is illustrated. As shown, the system 300 comprises an item of apparel 302 having one or more electronic devices 304 and a tag 110 with a scannable code 210. The one or more electronic devices 304 are in communication over a network 306 with a tag reader/scanner 308 via a transceiver 310. The tag reader 308 is further configured to read the scannable code 210 printed on the tag 110 via an interface 318 (as indicated by the dashed line therebetween).

As will be discussed in greater detail below, the apparel item 302 comprises so-called "smart" apparel and comprises one or more electronic devices 304. In one specific embodiment, at least one electronic device 304 comprises a sensor apparatus configured to obtain measurements relating to a user's performance of an activity. In another embodiment, the electronic device comprises a Near Field Communication (NFC) tag or other apparatus configured to simply receive and store data (e.g., identification data read from the scannable code 210 discussed herein).

As will be discussed in greater detail below, the scanner 308 comprises a storage apparatus or memory 314 which is configured to temporarily store data received from the interface 318 upon scanning the scannable code 210. For example, when the scanner 308 is used to scan the scannable code 210 of the tag 110, the data represented by the scannable code 210 (i.e., the data string 204) is acquired and stored at the scanner memory 314.

Once the data is obtained and stored 314, it is transmitted from the scanner 308 via the transceiver 316 to a transceiver 310 associated with the one or more electronic devices 304. In this manner data stored temporarily at the scanner memory 314 may be provided for storage at the electronic device memory 312 (as indicated by the dashed line therebetween). Once the data is transmitted the scanner memory 314 may purge the data; alternatively, the data is stored for a predetermined amount of time or until space in the memory is needed (as a first in/first out purging process).

The transceivers 316 and 310 as discussed above, enable transmission and receipt of data between the devices to which each is associated. These transceivers 316 and 310 may be any of various devices configured for communication with other electronic devices, including the ability to send communication signals and receive communication signals. They may include different types of transceivers configured to communicate with different networks and systems. Such transceivers are well known and will be recognized by those of ordinary skill in the art, including e.g., wireless telephony transceivers, Wi-Fi transceivers, Bluetooth® transceivers, or any of various other transceiver devices.

Similar to networks discussed previously, it is noted that the network 306 which enables communication between the electronic device(s) 304 and the scanner 308 may comprise one or more wired and/or wireless, private and/or public network, including but not limited to, e.g., the Internet. For example, the network 306 may comprise a wireless local area network (WLAN), wireless wide area network (WWAN), wired network, or any other suitable communication channel. Accordingly, the transceivers 310 and 316 are configured with appropriate networking communication interfaces. An example of wired communication interface may include, but is not limited to, Ethernet; while examples of wireless communication interfaces may include, but are not limited to, near field communication (NFC), Bluetooth, Wi-Fi, 4G or 5G LTE. It is further appreciated that various gateways, routers, switches, base stations, and so forth may be involved in facilitating and forwarding communication between the foregoing devices. Additionally, it is noted that the foregoing network may comprise several networks, such that the described components are distributed in various ones thereof. In alternative embodiments software via software API's. Additional mechanisms for further utilizing the tag are illustrated in FIG. 4 and described below.

Figure 4:
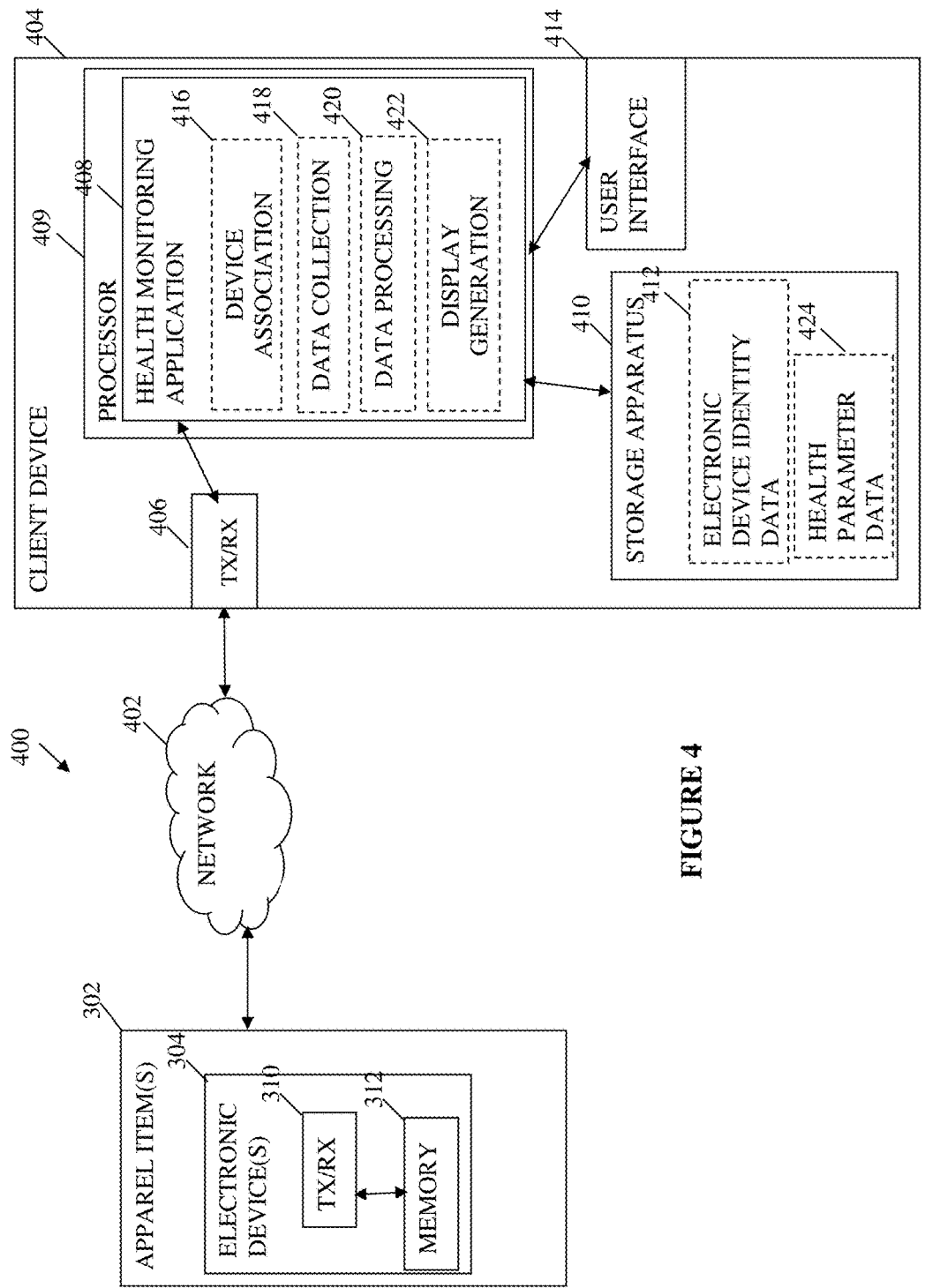
FIG. 4 is a block diagram illustrating an exemplary system for enabling one or more electronic devices of an item of apparel to be linked to a health monitoring application running at a client device in accordance with one embodiment of the present disclosure.

FIG. 4 illustrates an exemplary system 400 for enabling one or more electronic devices 304 of an item of apparel 302 to be linked to a health monitoring application 408 running at a client device 404. As shown, the system 400 comprises the electronic device(s) 304 of the apparel item 302 in communication with the client device 404 via a network 402.

As shown, the apparel 302 comprises one or more electronic devices 304 including e.g., processors, memory, and/or sensors associated therewith, attached thereto, and/or integrated therein. In the given example, the electronic device 304 comprises a transceiver apparatus 310 and a storage device 312. According to this embodiment, the electronic device(s) 304 further comprises one or more sensors configured to measure, obtain, monitor, generate, collect, sense, or otherwise receive biometric, environmental, movement, activity and/or health data. In order for the data to be reviewable by the user, the electronic device(s) 304 are linked to a health monitoring application 408 running at a user device 404.

The link or association between the health monitoring application 408 at the user device 404 and the electronic device(s) 304 at the item of apparel 302 is facilitated via a network 402. More specifically, a transceiver apparatus 406 of the user device 404 communicates to the transceiver device 310 of the electronic component 304 of the item of apparel 302 over the network 402.

Similar to the networks discussed previously, it is noted that the network 402 which enables communication between the electronic device(s) 304 and the user device 404 may comprise one or more wired and/or wireless, private and/or public network, including but not limited to, e.g., the Internet. For example, the network 402 may comprise a wireless local area network (WLAN), wireless wide area network (WWAN), wired network, or any other suitable communication channel. Accordingly, the transceivers 310 and 406 are configured with appropriate networking communication interfaces. An example of wired communication interface may include, but is not limited to, Ethernet; while examples of wireless communication interfaces may include, but are not limited to, near field communication (NFC), Bluetooth, Wi-Fi, 4G or 5G LTE. It is further appreciated that various gateways, routers, switches, base stations, and so forth may be involved in facilitating and forwarding communication between the foregoing devices. Additionally, it is noted that the foregoing network may comprise several networks, such that the described components are distributed in various ones thereof. In alternative embodiments software via software API's.

As described above with respect to FIG. 3, the memory 312 of the electronic device 304 of the item of apparel 302 has stored thereon information which uniquely identifies the item of apparel 302. In one embodiment, the information includes purchase order date, purchase order number, model identifier, color identifier, size, and serial number. It is appreciated that additional information may be stored at the electronic device 304 memory 312 relating to the item of apparel, the electronic device 304, the purchase order, etc. Such additional information may include information placed at the memory 312 during manufacture of the electronic device 304, or downloaded thereto from one or more other apparatus (not shown) as the item of apparel 302 is being manufactured.

The information obtained from the scannable tag 210 and stored into the memory 312 is broadcast by the electronic device 304 to enable association of the device 304 to the health monitoring application 408. As will be discussed in greater detail below, the apparel 302 broadcasts the information from the scannable tag 210 when one or more electronic devices 304 thereof determine that the apparel 302 should "awaken" from a low power state. The broadcast is picked up by the client device 404; and the information transmitted in the broadcast is then used to identify or recognize the item of apparel 302 during a sensor association process (discussed in further detail below).

As illustrated in FIG. 4, the exemplary client device 402 comprises a transceiver apparatus 406, a processor 409, a storage apparatus 410, and a user interface 414.

The user devices 404, in one exemplary implementation, comprise one or more portable computerized devices which are configured to measure, obtain, monitor, generate, collect, sense, or otherwise receive biometric, environmental, activity and/or health parameters. User devices 404 may also be referred to herein as health and/or activity monitoring devices, or client devices. In one variant, the client device 404 may comprise a smart phone, smart watch, other wearable device, and/or other portable electronic device that is configured to receive data relating to a user's activity. In one embodiment, the client device 404 may comprise one or more activity or health monitoring sensors for collecting data relating to the user's activity. Alternatively, the client device 404 may be in communication with one or more devices having sensors for collecting such data and transmitting the data to the client device 404.

The transceiver 406 is configured to send data from and receive data at the client device 404. For example, the transceiver 406 may receive data transmitted by the transceiver 310 of the apparel item 302, such as the previously referenced broadcast thereby. The transceiver 406 may further transmit data such as to a network server for storage of the data and/or other devices (not shown) in communication therewith. As shown, communication is therefore enabled between the client device 404, and the apparel tag electronic device 304 as discussed herein.

The transceiver 406 may be any of various devices configured for communication with other electronic devices, including the ability to send communication signals and receive communication signals. The transceiver 406 may include different types of transceivers configured to communicate with different networks and systems. Such transceivers are well known and will be recognized by those of ordinary skill in the art. In some embodiments, the transceiver 406 includes at least one transceiver configured to allow the user device 404 to perform wireless communications with the cell towers of the wireless telephony network, as will be recognized by those of ordinary skill in the art. The wireless telephony network may comprise any of several known or future network types. For example, the wireless telephony network may comprise commonly used cellular phone networks using CDMA, GSM or FDMA communication schemes, as well as various other current or future wireless telecommunications arrangements. In some embodiments, the transceiver 406 includes at least one transceiver configured to allow the user device 404 to communicate with any of various local area networks using Wi-Fi, Bluetooth® or any of various other communications schemes.

The storage apparatus 410 of the exemplary user device 404 in FIG. 4 is configured to store local copies of e.g., collected health parameter data 424 (received from e.g. a monitoring devices and/or input by a user), a client-side version of the herein described computer applications (including in one variant the illustrated health monitoring application 408), data relating to the electronic device identity 412, workout logs, social media posts, and/or any other locally created or stored data.

The processor 409 is configured to execute at least a health monitoring application 408 thereon. The health monitoring application 408 may be downloaded via a network interface from a web-based server, or alternatively be pre-installed on the device 404 at purchase. The health monitoring application 408 comprises a plurality of instructions which are configured to, when executed by the processor 409, enable the device 404 monitor, sense or otherwise obtain data relating to the user's participation in an activity. In one specific embodiment, the health monitoring application 408 is specifically configured for use with the electronic device 304 of the item of apparel 302 such that activity may be tracked when the user is wearing the apparel 302. The health monitoring application 408 comprises a plurality of functional applications including a device association application 416, a data collection application 418, a data processing application 420, and a display generation application 422. Each of these will be discussed in turn below.

The device association application 416 comprises a plurality of instructions which are configured to, when executed by the processor 409, enable the association of a specific electronic device 304 to the health monitoring application 408. Specifically, as will be discussed in greater detail below, the device association application 416 receives device identification information broadcast by the electronic device 304. Then, with this information scans an area to identify that the electronic device 304 is within range to establish a connection. The connection establishment may utilize methods similar to those employed during Bluetooth® pairing and will not be discussed in further detail herein.

The data collection application 418 comprises a plurality of instructions which are configured to, when executed by the processor 409, collect, sense, monitor, and/or otherwise obtain health parameter related data. In one embodiment, the data collection application enables the health monitoring application, such as e.g., UA Record™, MapMyFitness®, MyFitnessPal®, Endomondo®, etc. each owned by assignee hereof, to display health related data. Other health activity related monitoring applications may additionally be utilized as well. It is appreciated that the data collection application 418 may comprise a series of additional components necessary for the separate function of data collection, including e.g., communication components, sensor components, etc. (not shown). In another variant, the data collection application 418 receives some or all health parameter data from a separate monitoring devices (such as the electronic device(s) 304 of the item of apparel 302) and/or from an input by the user (such as via the user interface 414).

The data processing application 420 comprises a plurality of instructions which are configured to, when executed by the processor 409, process the raw health parameter data. In one embodiment, the raw data may include e.g., a number of steps taken (such as when the electronic device 304 comprises an accelerometer disposed in a shoe); according to this embodiment, the data processing application 420 causes additional data to be derived from the step data such as distance, pace, speed, etc. Similarly, the data processing application 420 may derive additional data using a plurality of data from one or more distinct sensor types or sources.

The display generation application 422 comprises a plurality of instructions which are configured to, when executed by the processor 409, enable the generation of a plurality of displays to be presented to a user via the user interface 414, as discussed herein. Specifically, one or more user interfaces may be generated which display the collected health-related data (both processed and raw), an affirmation or error relating to the association of the electronic device 304 to the application 408, other content (such as coaching or guidance), etc.

It is appreciated that the user device 404 may comprise additional applications (not shown) which contribute to the functioning thereof as described herein and/or the foregoing functionality may be distributed across more applications or combined into fewer applications. These and other components of the user device 404 will be clear to a person of ordinary skill in the art given the discussion of the functionality herein.

In one embodiment, the aforementioned processing is performed via coordination of a distributed application having client and network-side components. The network-side component may be run at a network entity or server and the client-side component run at the user device 404.

The herein-described applications enable uniform identification of various user activities as discussed throughout the disclosure and include e.g., the health monitoring application 408, the device association application 416, the data collection application 418, the data processing application 420, and the display generation application 422. A permanent copy of the programming instructions for these applications may be placed into permanent storage devices (such as e.g., the storage apparatus 410) during manufacture of the user device 404, or in the field, through e.g., a distribution medium (not shown), such as a compact disc (CD), or from a distribution server (not shown) via a network. That is, one or more distribution media having an implementation of the agent program may be employed to distribute the agent and program various computing devices.

The herein described applications improve the functioning of the user device 404 by enabling it to associate an item of apparel to a user's profile in a health monitoring application. Devices that are able to provide a means for association as disclosed herein can operate to more efficiently begin data collection from a plurality of electronic devices at the item of apparel and transmission of data collected therefrom to the user device.

Exemplary methods of (i) generating tags with scannable codes; (ii) associating data from a tag to an electronic device; (iii) enabling apparel to be linked to a health monitoring application; and (iv) utilizing connected apparel are discussed in further detail below.

Methodology

Figure 5:
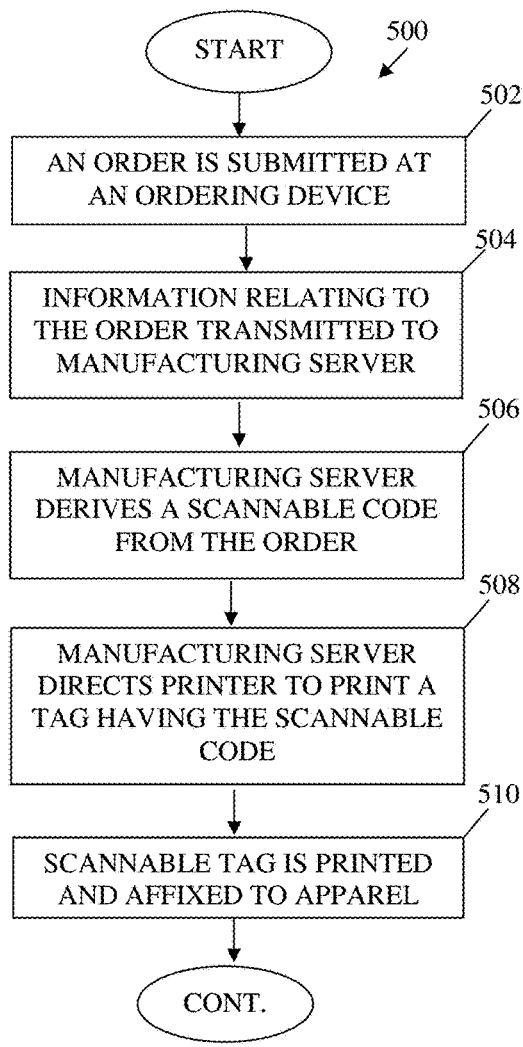
FIG. 5 is a logical flow diagram illustrating an exemplary method for generating tags for apparel having scannable codes printed thereon in accordance with one embodiment of the present disclosure.

Referring now to FIG. 5, a logical flow diagram illustrating an exemplary method 500 for generating tags for apparel having scannable codes printed thereon is given. As shown, per step 502 of the method, an order is submitted via an ordering device 102. As noted above, the ordering device may comprise any computerized apparatus usable by the user to place an order for apparel. For example, the device may comprise a personal or laptop computer; in another variant, the ordering device 102 may comprise the user device 404 discussed elsewhere herein. As discussed above, the order may be placed via a web site associated to the apparel manufacturer or apparel brand. For example, the user may use the ordering device 102 to connect to e.g., www.underarmour.com; from there he/she may select one or more items of apparel to purchase. In another example, the ordering device 102 may comprise a telephone which is used to place a call to an ordering center. According to this example, a purchase order is created at the ordering center, as discussed herein. Alternative mechanisms for enabling a user to purchase apparel may be used with equal success.

According to the present disclosure, the order which is placed comprises at least: information relating to the item of apparel to be purchased, credit card or other payment information, and shipping information. The information relating to the item to be purchased includes size, color, and item identification information (such as serial number and/or model number), etc. The purchase order further comprises information identifying the purchase order such as a purchase order date and purchase order number. Additional information may be provided in the purchase order, which is not discussed herein; the foregoing is merely exemplary of the overall features of the present disclosure.

The purchase order is provided to one or more appropriate servers for processing and fulfillment of the order. As shown, per step 504, information relating to the order is provided to the manufacturing server 106. In one variant, all of the information obtained during generation of the purchase order (i.e., the entire purchase order) is provided to the manufacturing server 106. The manufacturing server 106 then parses the data into that which is and that which is not necessary for the creation of the scannable code (discussed in detail below). Alternatively, only that information which is necessary for creation of the scannable code is provided to the manufacturing server 106. According to this embodiment, data which is not required at the manufacturing server 106 is not provided thereto (instead is provided to one or more other entities which require the information). In yet another variant, the information is provided directly to the manufacturing server 106 from the ordering device 102. Alternatively, the ordering device 102 may provide the purchase order information to a network server or other entity, which in turn provides only the relevant data to the manufacturing server 106.

Next, per step 506, the manufacturing server 106 derives a scannable code from the information provided in the purchase order. In one embodiment, as discussed elsewhere herein, the manufacturing server 106 uses the data to create a data string 204 defining the scannable code. Alternatively, or in addition, the manufacturing server 106 may further derive the scannable code 210 itself.

The manufacturing server 106 directs the printer 108 to print the scannable code 210 onto a tag 110 at step 508. This may occur via the manufacturing server 106 providing the scannable code 210 to the printer 108 for printing (step 510). Alternatively, in the instance the data string 204 is created, the printer 108 is configured to receive and decipher the string 204, and then use the information contained therein to generate the scannable code 210 and cause it to be printed (step 510) onto the tag 110. In one exemplary embodiment, the tag 110 comprises a fabric tag; alternatively, the tag 110 may comprise a plastic or sticker. The tag 110, once printed, is affixed to the item off apparel 302 to which it relates. That is, the information from the purchase order, as noted above, defines a specific item of apparel 302, hence the tag 110 once created is affixed to that item 302.

Figure 6:
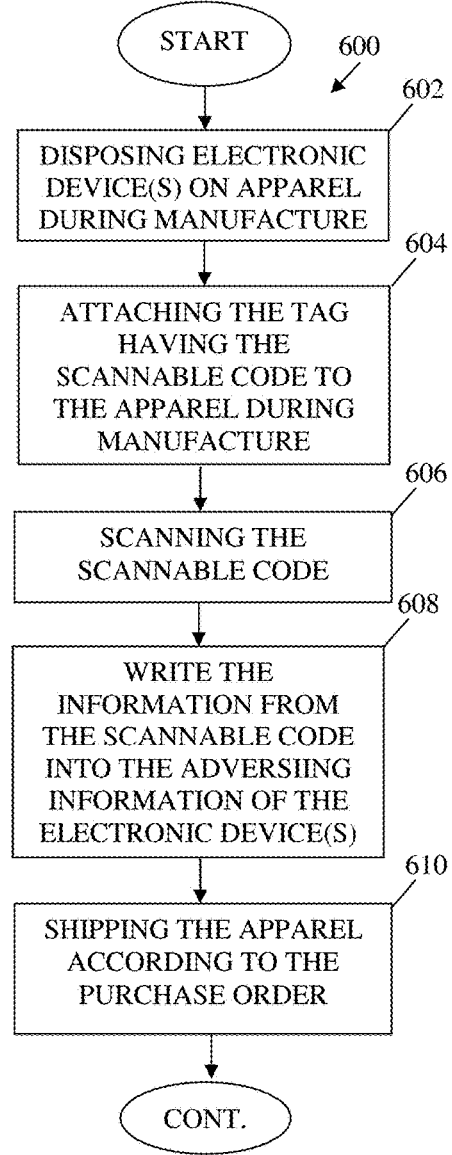
FIG. 6 is a logical flow diagram illustrating an exemplary method for automatically associating data contained within the apparel tag to one or more electronic devices of an apparel item in accordance with one embodiment of the present disclosure.

Referring now to FIG. 6, a logical flow diagram illustrating an exemplary method 600 for automatically associating data contained within the apparel tag 110 to one or more electronic devices of an apparel item 302 is given. As shown, per step 602, one or more electronic devices 304 are affixed to an item of apparel 302 during manufacture thereof. In one exemplary embodiment, the electronic devices 304 comprise one or more health and/or activity monitoring sensors. For example, the electronic devices 304 may comprise one or more of the following: pedometers, heart rate monitors, step counters, accelerometers, etc. In another embodiment, the apparel 302 comprises a shoe. It is appreciated however, that the apparel 302 may comprise any number of other items of clothing or wearable items, including e.g., shirts, pants, shorts, sports bras, compression garments, headbands, arm bands, chest bands, eye wear, wrist worn devices or apparel, etc.

In one specific variant, the electronic device 304 comprises a pod-type sensor inserted in a shoe (apparel 302). It is appreciated that the pod sensor may be disposed within a midsole region of the shoe. The disposal thereof in the midsole, per step 602, may conclude with the pod sensor being sealed within the midsole in one variant.

Next, at step 604, the tag 110 having the scannable code 210 thereon is attached to the article of apparel 302 during manufacture thereof. As noted above, the tag 110 may comprise a fabric tag or other material which is affixed to the item 302. It is appreciated that the tag is ideally placed in such a location on the item of apparel 302 that it does not interfere with normal wear thereof. For example, when the apparel item 302 comprises a shoe, the tag 110 may be placed on a tongue of the shoe; when the apparel item 302 comprises a shirt, the tag may be placed on an interior surface at a seam, near the hips of the wearer (and/or behind the neck of the wearer).

Once the item 302 has completed manufacture, various tests are performed. Certain tests are established to ensure the item of apparel 302 itself is manufactured correctly and able to function for its intended purpose (i.e., quality assurance). The testing may also include various tests to ensure that the electronic device(s) 304 are working properly. Such tests may vary based on the electronic device 304 and/or apparel 302 type and will not be discussed herein.

At step 606, the scannable code 210 on the fabric tag 110 is scanned using a scanning device 308. In one embodiment, step 606 may occur during the aforementioned testing process. The scanner 308 is operated by an operator at the place of manufacture of the item of apparel 302. Alternatively, the manufactured apparel 302 may be provided to a separate location for testing of the electronic devices 304 therein. Upon scanning (step 606), information stored in the scannable code 210 is written to storage 312 at the electronic device 304. In one variant, the information stored in the scannable code 210 (i.e., information which uniquely identifies the item of apparel 302) is stored as advertising information of the electronic device 304. That is, as will be discussed in greater detail below, the information is placed into a specific storage location identified specifically for information which will be advertised by the electronic device 304. In an alternative embodiment, however, the information may be stored, but not advertised.

Finally, at step 610, the apparel 302 is shipped according to the purchase order. As noted above, shipping information may be obtained and collected with regard to the purchase order. The manufacturing server 106 may store the shipping information until the item of apparel 302 is completed all steps of the manufacturing process, in one embodiment. Additional mechanisms for associating shipping information to a particular item of apparel 302 may be utilized with equal success; for example, the entire purchase order may be printed and associated to the item as it is being manufactured.

Figure 7:
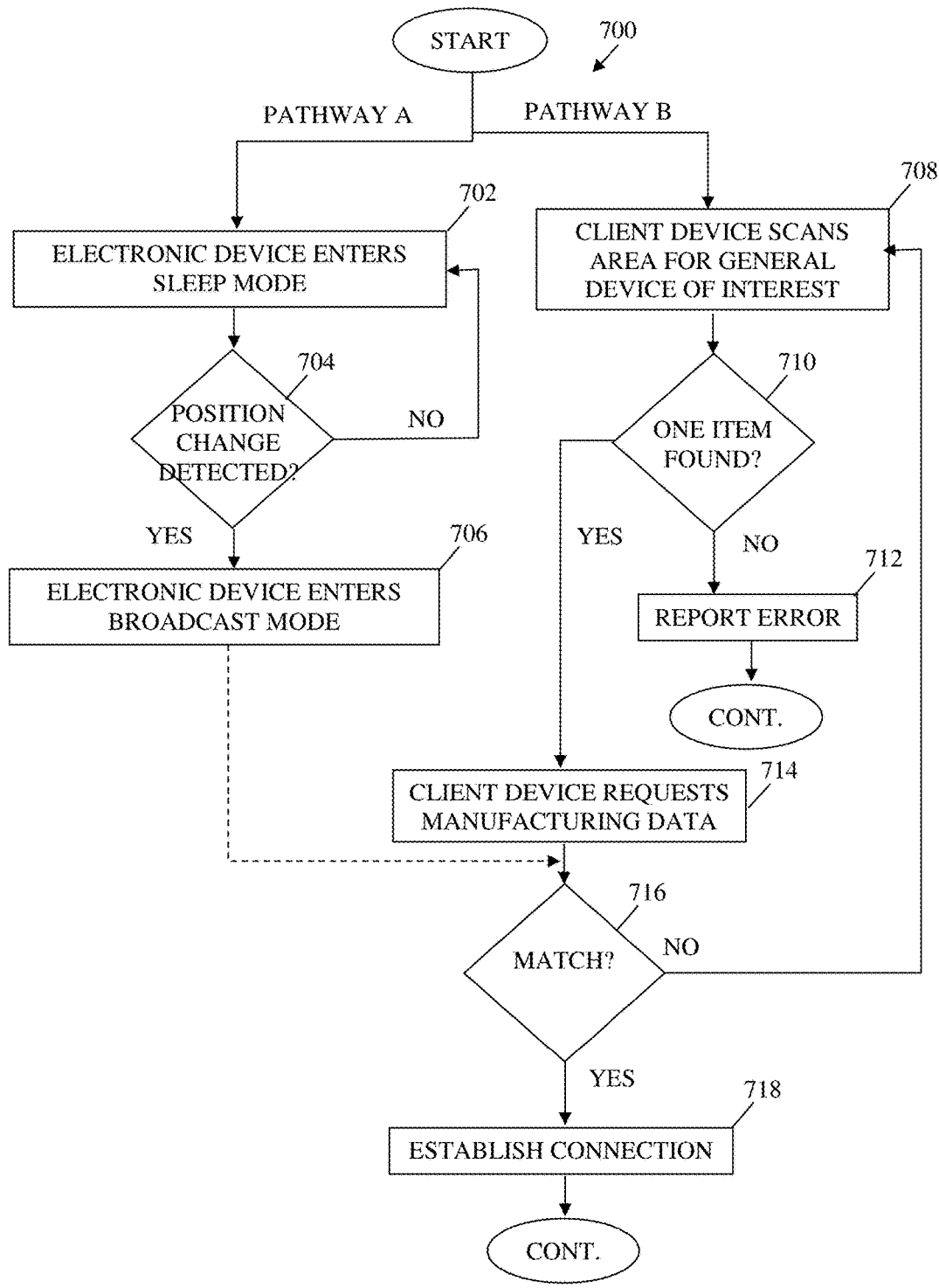
FIG. 7 is logical flow diagrams illustrating an exemplary method for enabling one or more electronic devices of an item of apparel to be linked to a health monitoring application running at a client device in accordance with one embodiment of the present disclosure.

Referring now to FIG. 7, a logical flow diagram illustrating an exemplary method 700 for enabling one or more electronic devices 304 of an item of apparel 302 to be linked to a health monitoring application 408 running at a client device 404 is given. The method 700 comprises two pathways, Pathway A and Pathway B, for the electronic device 304 and client device 404 respectively. It is appreciated that these pathways may run or be performed simultaneously or in any order.

Per pathway A, at step 702, the electronic device 304 enters a sleep mode. In one embodiment, the device 304 enters the sleep mode after manufacture of the item of apparel 302 upon detection of an absence of movement for a given amount of time. In another further embodiment, the positioning of the electronic device 304 (e.g., substantially horizontal, substantially vertical, etc.) is also used as an indicator that the device 304 should enter and/or remain in the sleep mode.

At step 704, it is determined whether a position of the electronic device 304 is changed. The position change is identified in one embodiment via the placement of sensors with respect to one another and/or with respect to a provided axis or plane. The sensors used to detect the position change may comprise accelerometers and the position change itself may be further coupled to acceleration changes in one embodiment. For example, the acceleration may be required to meet a given threshold and/or continue for a given period of time before the system will consider the acceleration to have been "detected" in one variant. For example, at least 1G of acceleration must be measured in order to "detect acceleration". In yet another variant, the accelerometer awakens every given interval (e.g., every 1 second, 5 seconds, etc.). When such acceleration is not detected (i.e., the threshold and/or duration are not met), the electronic device 304 returns to (or remains in) the sleep mode (step 702).

When the position change is detected, per step 706, the electronic device enters a broadcast mode. In the broadcast mode, the electronic device 302 may optionally look for nearby devices. If no nearby devices are identified, the electronic device 304 re-enters the sleep mode. In another embodiment, it is further determined whether the electronic device 304 is in an appropriate position to be awakened. In other words, the electronic device 304 comprises one or more sensors configured to determine an orientation of the apparel 302. In the instance the apparel 302 comprises a shoe; the positioning appropriate for waking the electronic device 304 is detected when the shoe is in a sole down, flat position. When the shoe of this example is positioned toe up, toe down, or heel up (i.e., upside down), the device is not considered to be in an appropriate position. Similar logic applies to other items of apparel 302 and electronic device 304 types.

During the broadcast mode, (step 706), the electronic device 304 broadcasts a self-identity to all nearby devices. In one embodiment, the broadcast is made over traditional wireless mechanisms include but not limited to, radio frequencies, Bluetooth®, etc. to all client devices in the area (such as e.g., client device 404). In one variant, the electronic device 304 broadcasts some or all of the information which was written to its memory 312 from the scannable code 210 (see e.g., FIG. 6, steps 606-608). Alternatively, the electronic device 304 merely broadcasts itself as a particular type of device (e.g., Run Speed Cadence or RSC device) and may include a generic name such as "Footpod".

Referring now to Pathway B, at step 708 the client device 404 scans an area for a general device of interest. For example, the user may have identified (e.g., at a device connection interface of the health monitoring application) that a specific item should be added to his/her registered devices. In one specific example, a pair of shoes may be identified generally as having been added. The client device 404 scans an immediate area (as defined by NFC, Bluetooth, or other wireless communications protocol) for a pair of shoes.

When more than one matching item is found or no matching items are found (step 710), the method proceeds to step 712 wherein an error is reported. In one embodiment, in response to receiving the error message, the client device 404 may retry to scan the area (step 708), enable the user to initiate a manual connection process, or simply time out.

When one item is found (step 710), the client device requests certain manufacturing data (step 714). The requested data may, in one instance comprise the data which was written to the device 304 memory from the scannable code 210, i.e., the data that was broadcast by the electronic device 304 when it is in broadcast mode (step 706). In this manner, the health monitoring application 408 is able to identify a shoe model, color and size by simply scanning the area and not directly connecting to a single or multiple shoes to provide identification and distinction.

At step 716, it is determined whether the identifying information comprises the device 404 which the user intended to connect. This may be determined by displaying at least some of the identifying information (which was provided during the self-identification broadcast) to the user for confirmation. When there is a match, the method 700 proceeds to step 718 wherein a connection is established between the client device 404 and the electronic device 304. The connection may comprise a Bluetooth® connection as discussed elsewhere herein. Alternatively, other connection types may be utilized with equal success. When there is not a match, the method may continue at step 708 and the client device rescans the area.

Figure 8:
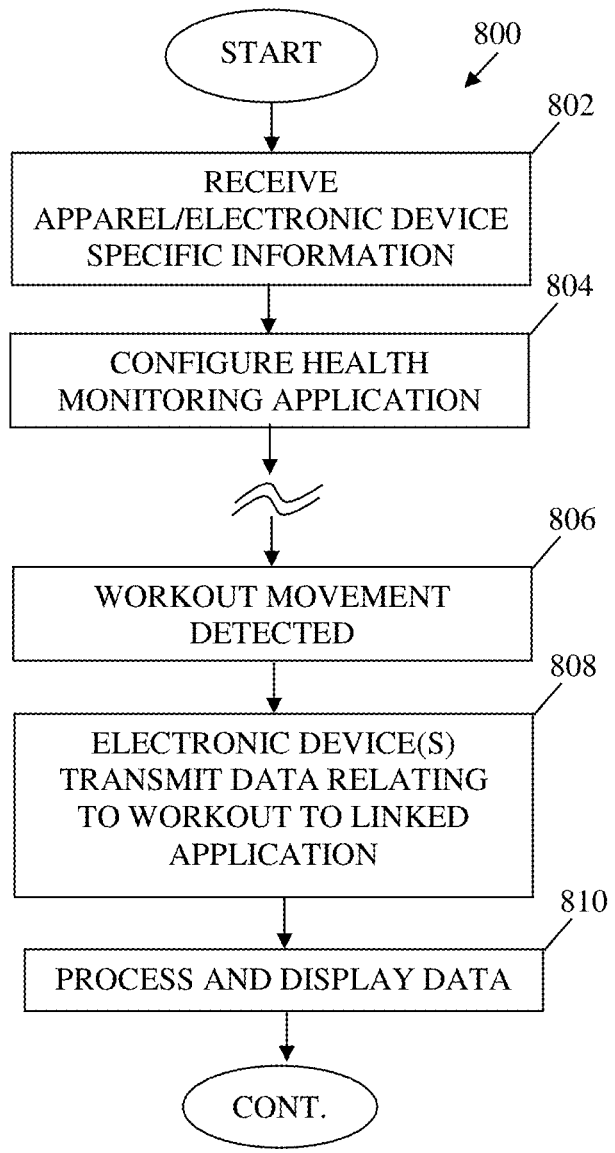
FIG. 8 is a logical flow diagram illustrating an exemplary method for utilizing apparel connected to a health monitoring application in accordance with one embodiment of the present disclosure.

Referring now to FIG. 8, a logical flow diagram illustrating an exemplary method 800 for utilizing apparel 302 connected to a health monitoring application 408 is given. As shown, per step 802, apparel 302 and/or electronic device 304 specific information is received at the client device 404. In one exemplary embodiment, the apparel 302 and/or device 304—specific information comprises the information obtained from the device 304 during the connection process (see FIG. 7, step 714). Accordingly, the information may comprise that information which was obtained from the purchase order, used to generate the scannable code 210, written into the memory of the electronic device 304 and provided to the client device 404. The information specifies, in one variant, a color, size, style or model, etc. of the apparel 302 as well as a type of electronic device 304 (e.g., accelerometer, pedometer, GPS, heart rate monitor, etc.).

The received information is used to configure the health monitoring application 408 (step 804). For example, once the model of the apparel 302 is known, the health monitoring application 408 may provide a picture of the apparel 302 in connection with the user's home screen or other display in the health monitoring application 408. Moreover, certain apparel types may have different color schemes, set of available screens, data displays, configurations, etc. Additionally, once the color of the apparel 302 is known, the health monitoring application 408 may provide a similar or matching color scheme throughout one or more of the displays of the application experience. Other features may be configured in accordance with the data describing the apparel 302 and/or devices 304, the foregoing being merely exemplary of the broader concepts.

After some period of time, workout movement is detected at the electronic devices 304 (step 806). The workout movement comprises raw data collected by the electronic devices which is known to be associated to a workout based on e.g., duration, meeting a threshold, etc. the electronic devices 304 transmit the data relating to the workout to the linked health monitoring application 408 at step 808. As is well known and will not be discussed herein, the health monitoring application 808 receives the raw data and processes it to generate one or more displays to the user (per step 810).

It will be appreciated that variants of the above-described and other features and functions, or alternatives thereof, may be desirably combined into many other different systems, applications or methods. Various presently unforeseen or unanticipated alternatives, modifications, variations or improvements may be subsequently made by those skilled in the art that are also intended to be encompassed by the following claims.

It will be appreciated that the various ones of the foregoing aspects of the present disclosure, or any parts or functions thereof, may be implemented using hardware, software, firmware, tangible, and non-transitory computer readable or computer usable storage media having instructions stored thereon, or a combination thereof, and may be implemented in one or more computer systems.

It will be apparent to those skilled in the art that various modifications and variations can be made in the disclosed embodiments of the disclosed device and associated methods without departing from the spirit or scope of the disclosure. Thus, it is intended that the present disclosure covers the modifications and variations of the embodiments disclosed above provided that the modifications and variations come within the scope of any claims and their equivalents.

What is claimed is:

1. A method of enabling shoe identification, comprising:
   receiving data used to create a machine-readable label, at a server apparatus, the machine readable label comprising at least information relating to a unique identity of one or more of a pair of shoes, the one or more of the pair of shoes comprising at least one physiological sensor configured for operation in a first mode and a second mode;
   the server apparatus causing a printer to print a fabric tag comprising at least the machine readable label based on the data, the fabric tag is attached onto a portion of the one or more of the pair of shoes during manufacture thereof;
   scanning the machine-readable label of the fabric tag at a testing device during the manufacture of the one or more of the pair of shoes, the testing device configured to test the functioning of the physiological sensor in association with the one or more of the pair of shoes, the act of scanning causing the information relating to the unique identity to be written to a storage device of the at least one physiological sensor at the one or more of the pair of shoes; and
   positioning the one or more of the pair of shoes in an orientation for shipping such that the physiological sensor enters the first mode, the physiological sensor configured to exit the first mode and enter the second mode upon detection of a change from the orientation for shipping.

2. The method of claim 1, wherein the information relating to the unique identity of the one or more pairs of shoes comprises one or more of: purchase order date, purchase order number, model identifier, color identifier, size, and serial number.

3. The method of claim 1, wherein the scanning occurs prior to a final test performed on the at least one physiological sensor by the testing device before completion of manufacture.

4. The method of claim 1, wherein the first mode is a sleep mode and the second mode is a broadcast mode, wherein the information relating to the unique identity is provided from the at least one physiological sensor to a user device during the second mode, the second mode including a process to automatically establish a connection between an application running at the user device and the at least one physiological sensor.

5. The method of claim 4, wherein the application running at the user device comprises a health monitoring application configured to process data relating to one or more exercise activities taken by a user of the pair of shoes.

6. The method of claim 1, wherein the act of receiving data used to create a machine-readable label comprises receiving data from an ordering device which initiated the purchase of the pair of shoes via a purchase order, and the information relating to a unique identity of one or more of a pair of shoes comprising information obtained at least in part from the purchase order.

7. The method of claim 1, wherein the at least one physiological sensor is disposed in a recess of a midsole portion of the one or more of the pair of shoes and sealed therein prior to completion of the manufacture thereof; and wherein the fabric tag is attached to an upper portion of the one or more of the pair of shoes.

8. A system for enabling apparel identification, said system comprising:
a code scanning apparatus configured to scan a machine-readable code printed onto a tag, the tag being attached to an item of apparel carrying a physiological sensor configured for operation in at least a first mode and a second mode, the code comprising at least information relating to a unique identity of the item of apparel, wherein the physiological sensor is configured to enter the first mode when the item of apparel is placed in an orientation for shipping and enter the second mode upon detection of a change of the item of apparel from the orientation for shipping;
a storage component configured to at least temporarily store the information relating to the unique identity of the item of apparel received via the scanning apparatus;
an apparel receiving apparatus configured to receive the item of apparel for testing; and
a processor in communication with the storage component and the apparel receiving apparatus and configured to execute at least one computer application thereon, said computer application comprising a plurality of instructions which are configured to, when executed, cause the apparel receiving apparatus to:
perform one or more tests with respect to the item of apparel and the physiological sensor while the item of apparel is received within the apparel receiving component, the one or more tests configured to test the functioning of the physiological sensor in association with the item of apparel by simulating physical activities to be performed by a user when wearing the item of apparel; and
cause the information relating to the unique identity of the item of apparel to be written to a memory of the physiological sensor of the item of apparel.

9. The system of claim 8, wherein the code scanning apparatus comprises a portable handheld device in communication with the apparel receiving apparatus, the processor and the storage component.

10. The system of claim 8, wherein the information relating to the unique identity of the item of apparel comprises information received from a purchase order created by a purchasing device in communication with a printer configured to use the information to print the machine-readable code onto the tag.

11. The system of claim 10, wherein the information relating to the unique identity of the item of apparel comprises one or more of: purchase order date, purchase order number, model identifier, color identifier, size, and serial number.

12. The system of claim 8, wherein the one or more tests configured to simulate physical activities to be performed by a user when wearing the item of apparel comprise tests to ensure proper functioning of the physiological sensor of the item of apparel during the simulated physical activities.

13. The system of claim 8, wherein the item of apparel comprises one or more shoes, the physiological sensor is mounted within a midsole portion of the one or more shoes, and the tag is attached to an upper portion of the one or more shoes.

14. A method for enabling apparel identification comprising:
scanning a machine-readable code printed onto a tag via a code scanning apparatus, the tag being attached to an item of apparel, the code comprising at least information relating to a unique identity of the item of apparel, and the item of apparel further comprising at least one sensor apparatus configured for operation in a first mode when in a first orientation and a second mode when in a second orientation;
temporarily storing the information relating to the unique identity of the item of apparel received via the code scanning apparatus at a storage component;
performing one or more tests while the item of apparel is received within an apparel receiving component, the one or more tests configured to ensure appropriate functioning of the sensor apparatus to measure one or more aspects of one or more physical activities of a wearer of the item of apparel;
causing the information relating to the unique identity of the item of apparel to be written to a memory of the sensor apparatus of the item of apparel at the apparel receiving component; and
positioning the item of apparel in the first orientation such that the sensor apparatus enters the first mode, wherein the first orientation is an orientation for shipping, wherein the sensor apparatus is configured to exit the first mode and enter the second mode upon detection of a change from the orientation for shipping.

15. The method of claim 14, wherein the information relating to the unique identity of the item of apparel comprises information received from a purchase order created by a purchasing device in communication with a printer configured to use the information to print the machine-readable code onto the tag.

16. The method of claim 14, wherein the sensor apparatus is further configured to advertise at least a portion of the information relating to the unique identity stored at the memory thereof.

17. The method of claim 16, wherein the sensor apparatus of the article of apparel is configured to connect to a health monitoring application run at a user device via the advertisement of the at least portion of the information relating to the unique identity.

18. The method of claim 17, wherein:
the sensor apparatus further comprises a transceiver device; and
the sensor apparatus is further configured to, once connected to the health monitoring application run at the user device, collect and transmit data relating to a user's physical activity.

19. The method of claim 14, wherein one or more tests comprise simulation of physical movement of the item of apparel.

* * * * *